(12) United States Patent
Haft et al.

(10) Patent No.: US 8,113,174 B2
(45) Date of Patent: Feb. 14, 2012

(54) METHOD FOR DETERMINING THE ETHANOL CONTENT OF THE FUEL IN A MOTOR VEHICLE

(75) Inventors: Gerhard Haft, Obermotzing (DE); Wolfgang Moser, Regensburg (DE)

(73) Assignee: Continental Automotive GmbH, Hannover (DE)

( * ) Notice: Subject to any disclaimer, the term of this patent is extended or adjusted under 35 U.S.C. 154(b) by 144 days.

(21) Appl. No.: 12/441,156

(22) PCT Filed: May 31, 2007

(86) PCT No.: PCT/EP2007/055322
§ 371 (c)(1),
(2), (4) Date: Aug. 4, 2009

(87) PCT Pub. No.: WO2008/031641
PCT Pub. Date: Mar. 20, 2008

(65) Prior Publication Data
US 2009/0308350 A1    Dec. 17, 2009

(30) Foreign Application Priority Data
Sep. 15, 2006  (DE) .......................... 10 2006 043 341

(51) Int. Cl.
*F02M 7/00*    (2006.01)
(52) U.S. Cl. .......................... 123/436; 123/1 A; 123/575

(58) Field of Classification Search .................. 123/1 A, 123/435, 436, 575, 576, 672, 689, 494; 701/102–104; 73/114.38
See application file for complete search history.

(56) References Cited

U.S. PATENT DOCUMENTS

| | | | |
|---|---|---|---|
| 4,059,411 A | 11/1977 | Smith | |
| 5,694,901 A * | 12/1997 | Togai et al. | 123/436 |
| 5,950,599 A | 9/1999 | Rotramel et al. | |
| 6,085,143 A | 7/2000 | Przymusinski et al. | |
| 6,206,940 B1 | 3/2001 | Weissman et al. | |
| 6,257,174 B1 | 7/2001 | Huff et al. | |
| 6,298,838 B1 | 10/2001 | Huff et al. | |
| 2008/0035119 A1* | 2/2008 | Marriott et al. | 123/494 |
| 2008/0295574 A1* | 12/2008 | Miersch-Wiemers et al. | 73/23.31 |
| 2009/0276143 A1* | 11/2009 | Rackmil et al. | 701/103 |

FOREIGN PATENT DOCUMENTS

| | | |
|---|---|---|
| DE | 19741965 C1 | 1/1999 |
| DE | 4122139 C2 | 7/2000 |
| DE | 60011393 T2 | 6/2005 |
| WO | WO 0198776 A1 | 12/2001 |

* cited by examiner

*Primary Examiner* — John T. Kwon
*Assistant Examiner* — Johnny Hoang
(74) *Attorney, Agent, or Firm* — King & Spalding L.L.P.

(57) ABSTRACT

A method for determining the Ethanol content of the fuel in a motor vehicle uses the dependence of the lean-running limit of the internal combustion engine on the ethanol content of the fuel to determine the ethanol content, by the fact that the ethanol content is arrived at from the required reduction in the injected fuel quantity to reach the lean-running limit.

11 Claims, 2 Drawing Sheets

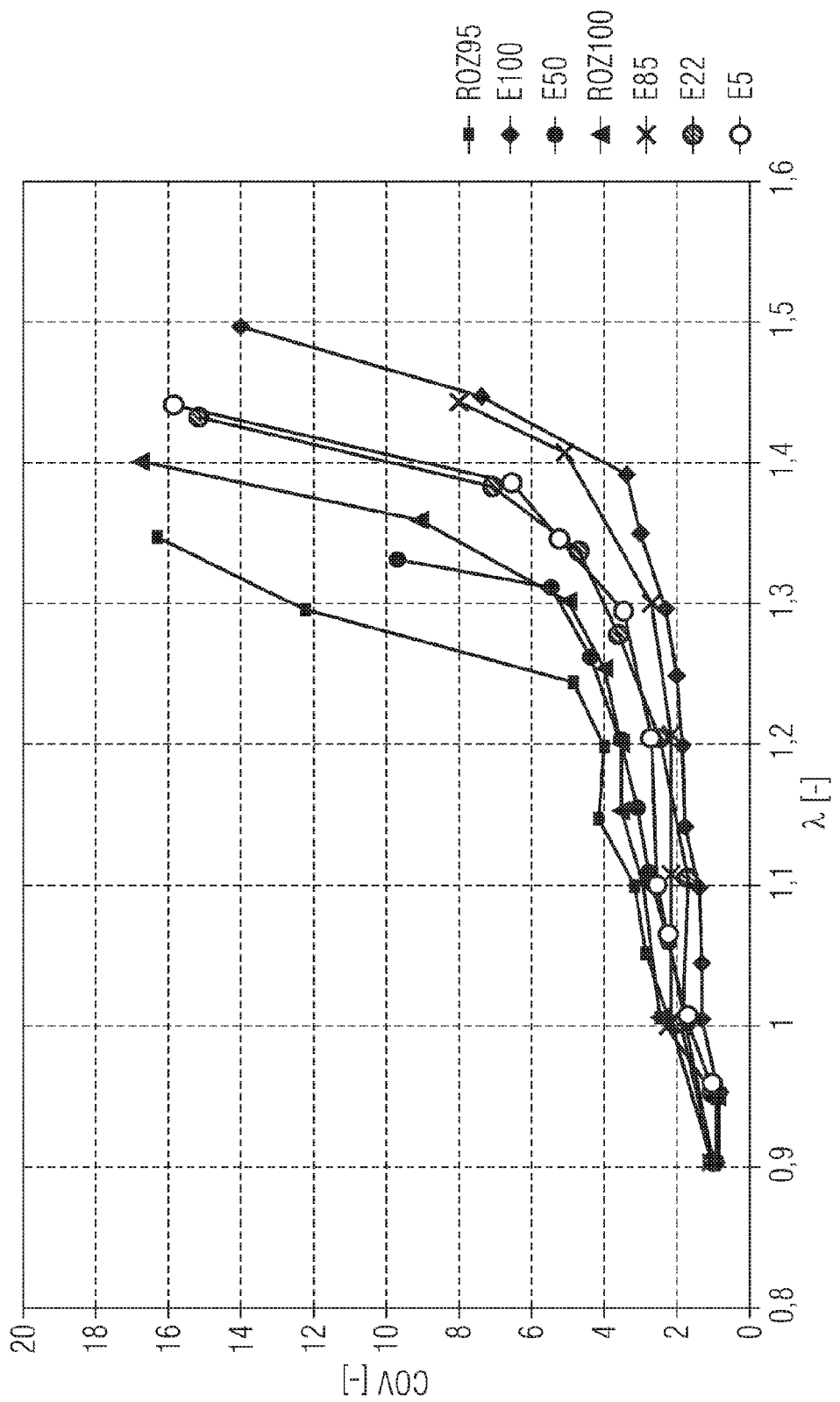

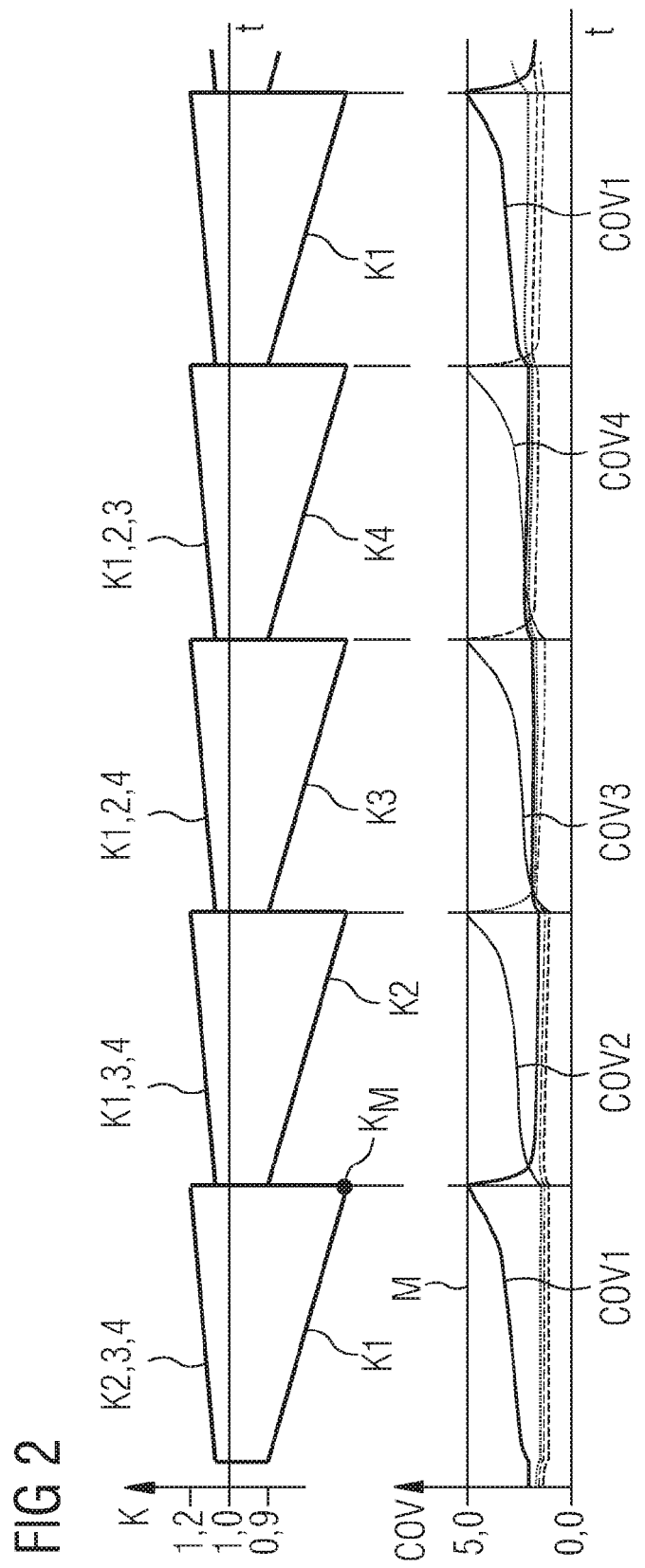

METHOD FOR DETERMINING THE ETHANOL CONTENT OF THE FUEL IN A MOTOR VEHICLE

CROSS-REFERENCE TO RELATED APPLICATIONS

This application is a United States national phase filing under 35 U.S.C. §371 of International Application No. PCT/EP2007/055322, filed May 31, 2007, which claims priority to German Patent Application No. 10 2006 043 341.6, filed Sep. 15, 2006. The complete disclosure of the above-identified applications is hereby fully incorporated herein by reference.

TECHNICAL FIELD

The present invention relates to a method for determining the Ethanol content of the fuel in a motor vehicle.

BACKGROUND

There have long been trials in operating motor vehicles with fuel containing Ethanol (Alcohol) and in South America and North America in particular many motor vehicles are equipped for such operation. The concentration of the Ethanol in the fuel in the tank can vary from filling to filling depending on the type of fuel put into the tank. In such cases any Ethanol content of the fuel between 0 and 100% can be produced. For trouble-free operation of the internal combustion engine it is necessary for the engine management device to detect the new fuel composition as soon as possible and take it into account in its regulation strategies.

In the prior art (see U.S. Pat. No. 6,257,174 B1 for example) it is already known that the different air requirement of Ethanol on the one hand and other fuels on the other hand (Ethane 8,9; Gasoline: 14,7) can be used to determine the Ethanol content of the fuel. When the Ethanol content of the fuel changes, the excess-air ratio $\lambda$ measured by the $\lambda$ sensor, and from this change in the excess-air ratio the Ethanol proportion of the fuel can be deduced ($\lambda$ method).

However the $\lambda$ method only enables the Ethanol content to be determined reliably when the fuel system is intact. Since the Fuel System Diagnosis (FSD) is likewise conducted by means of the $\lambda$ values measured by the $\lambda$ sensor, the $\lambda$ method does not provide any reliable $\lambda$ values. The engine management device can namely not establish uniquely whether a deviation of the $\lambda$ value is the result of a changed Ethanol content of the fuel or of a fault in the fuel system.

SUMMARY

According to various embodiments, a method for determining the Ethanol content of the fuel of a motor vehicle can be specified which is independent of a measurement of the excess-air factor $\lambda$ in the exhaust gas of the internal combustion engine.

According to an embodiment, a method for determining the Ethanol content of the fuel of a motor vehicle, may comprise the step of determining the Ethanol content by using the dependency of lean-running limit of the internal combustion engine of the motor vehicle on the Ethanol content of the fuel. According to a further embodiment, to determine the lean-running limit, the amount of fuel to be injected in a cylinder of the internal combustion engine can be progressively reduced, the coefficient of variance of the internal combustion engine is monitored for this cylinder during this process and the lean-running limit is recognized as reached if the coefficient of variance exceeds a predetermined threshold value. According to a further embodiment, the Ethanol content of the fuel can be deduced from the reduction of the quantity of fuel injected required to reach the lean-running limit. According to a further embodiment, during the reduction of the quantity of fuel injected into a cylinder, the amount of fuel injected into the remaining cylinders can be progressively increased so that the excess-air factor $\lambda$ is kept at a constant value. According to a further embodiment, the Ethanol content of the fuel may be obtained from an engine map in which the Ethanol content is plotted against the reduction of the injected fuel required to reach the lean-running limit. According to a further embodiment, the Ethanol content in the engine map can be plotted as a function of the speed and load of the internal combustion engine. According to a further embodiment, the lean-running limit can be determined for an operation of the internal combustion engine at a stationary load point. According to a further embodiment, the Ethanol content of the fuel can be used for validation of the Ethanol content obtained using another method.

BRIEF DESCRIPTION OF THE DRAWINGS

Further features and advantages of the method according to various embodiments are described with reference to the enclosed drawings. The figures are as follows:

FIG. 1 a diagram in which the coefficient of variance COV is plotted against the excess-air factor $\lambda$, and FIG. 2 two diagrams, with in the upper diagram a factor K for the amount of fuel to be injected being plotted over the time t and in the lower diagram the coefficient of variance COV being plotted over the time t.

DETAILED DESCRIPTION

The various embodiments are based on the knowledge that internal combustion engines operated with Ethanol exhibit an improved lean-running capability. This means that the lean-running limit of the internal combustion engine is moved in the lean direction as the Ethanol content of the fuel becomes greater. This relationship between lean-running limit and Ethanol content of the fuel will be used to determine the Ethanol content.

To determine the lean-running limit the amount of fuel to be injected into a cylinder of the internal combustion engine is progressively reduced, the coefficient of variance of the internal combustion engine for this cylinder monitored during this process and the lean-running limit recognized as having been reached if the coefficient of variance exceeds a predetermined threshold value. From the reduction in the amount of fuel required to reach the lean-running limit conclusion is then drawn—expediently using an engine map—as to the Ethanol content of the fuel.

The method according to various embodiments is especially used to validate the Ethanol content obtained using another method (especially the $\lambda$ method).

As already mentioned, the various embodiments make use of the fact that, with an increase of the Ethanol content of the fuel, the lean-running capability of the internal combustion engine improves. This relationship is shown by the diagram of FIG. 1, in which the Coefficient Of Variance (COV) is plotted against the excess-air factor $\lambda$ for different fuels. The dimensionless coefficient of variance COV characterizes the smooth running of an internal combustion engine; This means that the uneven running becomes greater as the coefficient of variance COV becomes greater. A predetermined threshold value (for example COV=5) is usually defined as the lean-running limit, above which acceptable smooth running of the internal combustion engine no longer obtains.

The ROZ95 and ROZ100 curves shown in the diagram of FIG. 1 apply for a gasoline with an octane number of 95 while the curves E5, E50, E85 and E100 curves apply to fuel with an Ethanol content of 5%, 50%, 85% or 100%.

As can be seen from the diagram of FIG. 1, the lean-running limit (COV=5) shifts as the Ethanol content of the fuel becomes greater in the direction of a greater excess-air factor $\lambda$, meaning in the lean fuel direction. Thus the lean-running limit for ROZ 95 gasoline lies at an $\lambda$ value of around 1.25, while the lean-running limit for pure Ethanol (E100) lies at an $\lambda$ value of around 1.42

Based on the diagram depicted in FIG. 2, the method in accordance with an embodiment will now be explained in connection with a four-cylinder internal combustion engine (not shown):

If the internal combustion engine is operated at a constant load point, e.g. idling, the amount of fuel injected into a first cylinder is first reduced in stages. This is shown in the upper diagram of FIG. 2 by a factor K for the amount of fuel to be injected. First of all the factor K1 is reduced for the first cylinder to 0.9 and then progressively further. At the same time the amount of fuel to be injected in the other cylinders is increased by a corresponding amount, so that the overall fuel/air-ratio of all cylinders is kept at $\lambda=1$. This is indicated in the upper diagram of FIG. 2 by the curves designated K2, K3 and K4.

At the same time as the described change in the amount of fuel to be injected the excess-air amount of the internal combustion engine for the individual cylinders is monitored. Since the monitoring of the excess-air amount is known in the prior art (cf. e.g. DE 41 22 139 and DE 197 41 965) it will not be discussed in any greater detail here. As shown in the lower diagram of FIG. 2, the coefficient of variance COV1 for the first cylinder becomes increasingly larger while the amount of fuel to be injected is reduced and thus the air/fuel mixture is made leaner, as can be seen through the curve COV1 in the lower diagram of FIG. 2.

In the exemplary embodiment shown the COV value representing the lean-running limit M is assumed to be 5. If the coefficient of variance COV1 for the first cylinder has now reached the lean-running limit M (COV=5) the factor $K_M$ assigned to the lean-running limit M amounts to 0.7 for the first cylinder for example. This factor $K_M$, which represents the reduction in the amount of fuel injected into the first cylinder on reaching the lean-running limit, now allows a determination of the Ethanol content of the fuel.

The Ethanol content is expediently read out from an engine map (not shown) in which the Ethanol content is plotted against the factor $K_M$. For practical reasons it can also be expedient to plot the Ethanol content against $\lambda_M$ in the engine map, with $\lambda_M = 1/K_M$. In the exemplary embodiment described for example $\lambda_M = 1/0.7 = 1.428$ then applies.

If the coefficient of variance COV1 has reached the lean-running limit M for the first cylinder the reduction in the amount of fuel to be injected is ended for the first cylinder. The described method of reducing the amount of fuel amount to be injected for the remaining cylinders is then carried out as is indicated in the two diagrams of FIG. 2. The Ethanol content of the fuel is then determined from a statistical evaluation of the results for all cylinders and by means of a number of passes of the described method.

As already mentioned at the start, the Ethanol content of the fuel determined in this manner is used to validate an $\lambda$ method known in the prior art. A significant advantage of the method in accordance with various embodiments lies in the fact that it does not depend on a measurement of the $\lambda$ value. This validation allows it to be determined at any time whether a change of the $\lambda$ value is based on a change of the Ethanol content or a fault of the fuel system. With the validated values of the $\lambda$ method the engine management system can carry out the current usual $\lambda$ adaption method and the Fuel System Diagnosis (FSD).

The invention claimed is:

1. A method for determining an Ethanol content of fuel of a motor vehicle having multiple cylinders, comprising:
    progressively reducing an amount of fuel injected into a first cylinder;
    during the reduction of the quantity of fuel injected into the first cylinder, progressively increasing an amount of fuel injected into the other cylinders of the motor vehicle to compensate for the reduced fuel injection into the first cylinder;
    monitoring a coefficient of variance for the first cylinder during the reduction of fuel injected into the first cylinder;
    identifying a limit point at which the coefficient of variance for the first cylinder reaches a predetermined lean-running limit;
    determining an amount of the fuel injection reduction at the identified limit point;
    determining the Ethanol content of the fuel based on the determined amount of fuel reduction at the identified limit point.

2. The method according to claim 1, wherein, during the reduction of the quantity of fuel injected into the first cylinder, the amount of fuel injected into the other cylinders is progressively increased so that an excess-air factor is kept at a constant value.

3. The method according to claim 1, wherein the Ethanol content of the fuel is obtained from an engine map in which the Ethanol content is plotted against the reduction of the injected fuel required to reach the lean-running limit.

4. The method according to claim 3, wherein the Ethanol content in the engine map is plotted as a function of a speed and load of the internal combustion engine.

5. The method according to claim 1, wherein the lean-running limit is determined for an operation of the internal combustion engine at a stationary load point.

6. The method according to claim 1, wherein the Ethanol content of the fuel is used for validation of the Ethanol content obtained using another method.

7. A system for determining an Ethanol content of fuel of a motor vehicle having multiple cylinders, comprising:
    means for progressively reducing an amount of fuel injected into a first cylinder;
    means for progressively increasing an amount of fuel injected into the other cylinders of the motor vehicle during the reduction of the quantity of fuel injected into the first cylinder to compensate for the reduced fuel injection into the first cylinder;
    means for monitoring a coefficient of variance for the first cylinder during the reduction of fuel injected into the first cylinder;
    means for identifying a limit point at which the coefficient of variance for the first cylinder reaches a predetermined lean-running limit;
    means for determining an amount of the fuel injection reduction at the identified limit point;
    means for determining the Ethanol content of the fuel based on the determined amount of fuel reduction at the identified limit point.

8. The system according to claim 7, wherein, during the reduction of the quantity of fuel injected into the first cylinder, the system is operable to increase the amount of fuel injected into the other cylinders progressively so that an excess-air factor is kept at a constant value.

9. The system according to claim 7, wherein the Ethanol content of the fuel is obtained from an engine map in which the Ethanol content is plotted against the reduction of the injected fuel required to reach the lean-running limit.

10. The system according to claim 9, wherein the Ethanol content in the engine map is plotted as a function of a speed and load of the internal combustion engine.

11. The system according to claim 7, wherein the system is operable to determine lean-running limit for an operation of the internal combustion engine at a stationary load point.

* * * * *